(12) United States Patent
Harms et al.

(10) Patent No.: US 9,149,584 B2
(45) Date of Patent: Oct. 6, 2015

(54) HINGED SHIELD ASSEMBLY AND RELATED METHODS

(75) Inventors: Volker Harms, Kassel (DE); Juergen Fuchs, Bad Emstal (DE); Markus Kaemereit, Nottuln (DE); Frank-Michael Roediger, Burgdorf (DE)

(73) Assignee: B. Braun Melsungen AG, Melsungen (DE)

( * ) Notice: Subject to any disclaimer, the term of this patent is extended or adjusted under 35 U.S.C. 154(b) by 906 days.

(21) Appl. No.: 13/129,789

(22) PCT Filed: Nov. 12, 2009

(86) PCT No.: PCT/US2009/064215
§ 371 (c)(1),
(2), (4) Date: Aug. 10, 2011

(87) PCT Pub. No.: WO2010/059502
PCT Pub. Date: May 27, 2010

(65) Prior Publication Data
US 2011/0288496 A1 Nov. 24, 2011

Related U.S. Application Data

(60) Provisional application No. 61/115,647, filed on Nov. 18, 2008.

(51) Int. Cl.
*A61M 5/32* (2006.01)

(52) U.S. Cl.
CPC .................................. *A61M 5/3216* (2013.01)

(58) Field of Classification Search
CPC . A61M 5/3205; A61M 5/321; A61M 5/3213; A61M 5/3216; A61M 5/3219; A61M 2005/3217

USPC .................. 604/192, 263, 110, 111, 197, 198
See application file for complete search history.

(56) References Cited

U.S. PATENT DOCUMENTS

| 5,405,332 A | * | 4/1995 | Opalek ......................... 604/192 |
| 5,599,313 A | * | 2/1997 | Gyure et al. .................. 604/192 |

(Continued)

FOREIGN PATENT DOCUMENTS

JP          2003-52820          2/2003

OTHER PUBLICATIONS

International Search Report completed Jul. 16, 2010 and mailed Jul. 20, 2010 from corresponding International Application No. PCT/US2009/064215; Filed Nov. 12, 2009 (6 pages).
Written Opinion completed Jul. 16, 2010 and mailed Jul. 20, 2010 from corresponding International Application No. PCT/US2009/064215; Filed Nov. 12, 2009 (5 pages).
International Preliminary Report on Patentability completed Jul. 16, 2010 and mailed Jun. 3, 2011 from corresponding International Application No. PCT/US2009/064215; Filed Nov. 12, 2009 (8 pages).

*Primary Examiner* — Kami A Bosworth
(74) *Attorney, Agent, or Firm* — Klein, O'Neill & Singh, LLP (57) ABSTRACT

The present hinged shield assembly is configured to shield a needle to prevent needlesticks. The assembly comprises a base including a hinge, a first shield and a second shield. The first shield extends from the base and at least partially surrounds the second shield. The first and second shields are configured to pivot about the hinge. In some embodiments a distal end of the first shield is open. In other embodiments the first and second shields include sidewalls with channels extending therealong. The first and second shields are rotatable with respect to one another such that the channels in each may be aligned. In other embodiments the first and second shields are translatable and rotatable with respect to one another.

19 Claims, 11 Drawing Sheets (56) References Cited

U.S. PATENT DOCUMENTS

| | | | |
|---|---|---|---|
| 5,632,732 A | | 5/1997 | Szabo et al. |
| 6,015,397 A | * | 1/2000 | Elson et al. .................. 604/192 |
| 6,869,418 B2 | | 3/2005 | Marano-Ford |
| 2002/0151852 A1 | | 10/2002 | Crawford et al. |
| 2006/0270979 A1 | | 11/2006 | Simas, Jr. et al. |
| 2008/0051724 A1 | * | 2/2008 | Bedford et al. ................ 604/192 |
| 2008/0269693 A1 | * | 10/2008 | Steube et al. ................. 604/198 |

* cited by examiner

HINGED SHIELD ASSEMBLY AND RELATED METHODS

CROSS-REFERENCE TO RELATED APPLICATIONS

This application is a national phase application of International Application No. PCT/US2009/064215, filed Nov. 12, 2009, entitled HINGED SHIELD ASSEMBLY AND RELATED METHODS, which claims the benefit of U.S. Provisional Application No. 61/115,647, filed Nov. 18, 2008, the contents of which are expressly incorporated herein by reference.

FIELD

The present invention relates generally to caps for needle devices, and more particularly to hinged cap devices for use with hypodermic needles.

BACKGROUND

Recapping is a common procedure for periods between drawing up fluids into a syringe and administering injections through a needle. The recapping procedure can occasionally cause needlesticks since users sometime misalign the needles with the openings on the caps. Needlesticks can be painful, but can also cause great inconvenience because all needlesticks must be reported. Also, since needles related to needlesticks must be discarded. medications contained within the syringes are unnecessarily wasted. Furthermore, fluids linked to these clean type of needlesticks can cause injuries and adverse reactions.

SUMMARY

The preferred embodiments of the present hinged shield assembly and related methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description of the Preferred Embodiments," one will understand how the features of the present embodiments provide advantages, which include the ability to lock the shield against further movement so that the needle contained within the shield cannot accidentally be re-exposed.

One embodiment of the present methods of shielding a needle to prevent needlesticks comprises rotating a first shield in a first direction with respect to a second shield. The method further comprises pivoting the first and second shields in a first direction with respect to the needle to expose a sharp distal tip of the needle. The method further comprises pivoting the first and second shields in a second direction with respect to the needle, opposite the first direction, until the needle is at least partially enclosed within the first and second shields. The method further comprises rotating the first shield in a second direction, opposite the first direction, with respect to the second shield. The method further comprises translating the first shield with respect to the second shield to lock the second shield against further rotational and translational motion with respect to the first shield.

One embodiment of the present hinged shield assembly is configured to shield a needle to prevent needlesticks. The assembly comprises a base including a hinge, a first shield and a second shield. The first shield extends from the base and at least partially surrounds the second shield. The first and second shields are configured to pivot about the hinge, and a distal end of the first shield is open.

Another embodiment of the present hinged shield assembly is configured to shield a needle to prevent needlesticks. The assembly comprises a base including a hinge, a first shield and a second shield. The first shield extends from the base and at least partially surrounds the second shield. The first shield includes a sidewall and a channel extending along the sidewall in a direction parallel to a longitudinal axis of the first shield. The second shield includes a sidewall and a channel extending along the sidewall in a direction parallel to a longitudinal axis of the second shield. The first and second shields are configured to pivot about the hinge, and the first and second shields are rotatable with respect to one another such that the channels in each may be aligned.

Another embodiment of the present hinged shield assembly is configured to shield a needle to prevent needlesticks. The assembly comprises a base including first and second spaced flanges and a hinge. The assembly further comprises a first shield and a second shield. The first shield extends from the base and at least partially surrounds the second shield. The first and second shields are configured to pivot about the hinge, and the second shield includes a tab that is selectively disposable within a space defined between the first and second flanges.

Another embodiment of the present hinged shield assembly is configured to shield a needle to prevent needlesticks. The assembly comprises a base including first and second spaced flanges and a hinge. The assembly further comprises a first shield and a second shield. The first shield extends from the base and at least partially surrounds the second shield. The first and second shields are configured to pivot about the hinge, and the second shield includes a tab that is selectively disposable within a channel that extends along a sidewall of the first shield in a direction parallel to a longitudinal axis of the first shield.

Another embodiment of the present hinged shield assembly is configured to shield a needle to prevent needlesticks. The assembly comprises a base including first and second spaced flanges and a hinge. The assembly further comprises a first shield and a second shield. The first shield extends from the base and at least partially surrounds the second shield. The first and second shields are configured to pivot about the hinge, and the first and second shields are translatable and rotatable with respect to one another.

BRIEF DESCRIPTION OF THE DRAWINGS

The preferred embodiments of the present hinged shield assembly and related methods now will be discussed in detail with an emphasis on highlighting the advantageous features. These embodiments depict the novel and non-obvious hinged shield assembly shown in the accompanying drawings, which are for illustrative purposes only. These drawings include the following figures, in which like numerals indicate like parts.

DETAILED DESCRIPTION

The following detailed description describes the present embodiments with reference to the drawings. In the drawings, reference numbers label elements of the present embodiments. These reference numbers are reproduced below in connection with the discussion of the corresponding drawing features.

Figure 1:
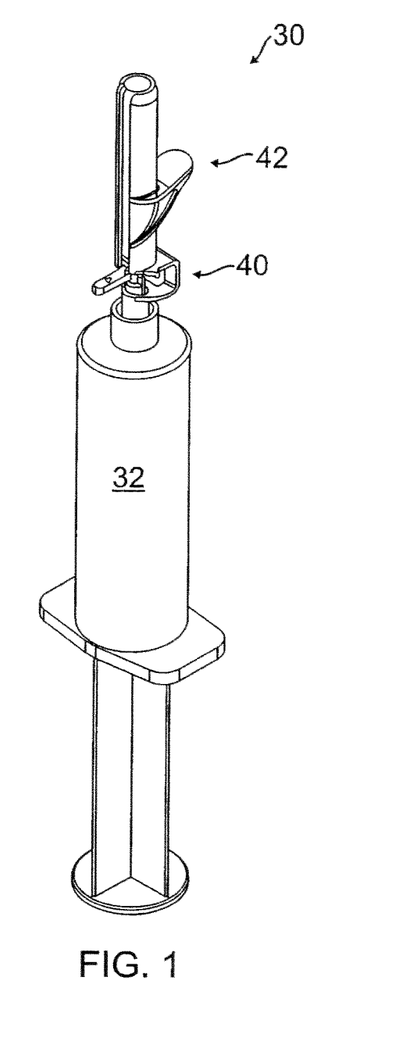
FIG. 1 is a front perspective view of one embodiment of the present hinged shield assembly.
Figure 5:
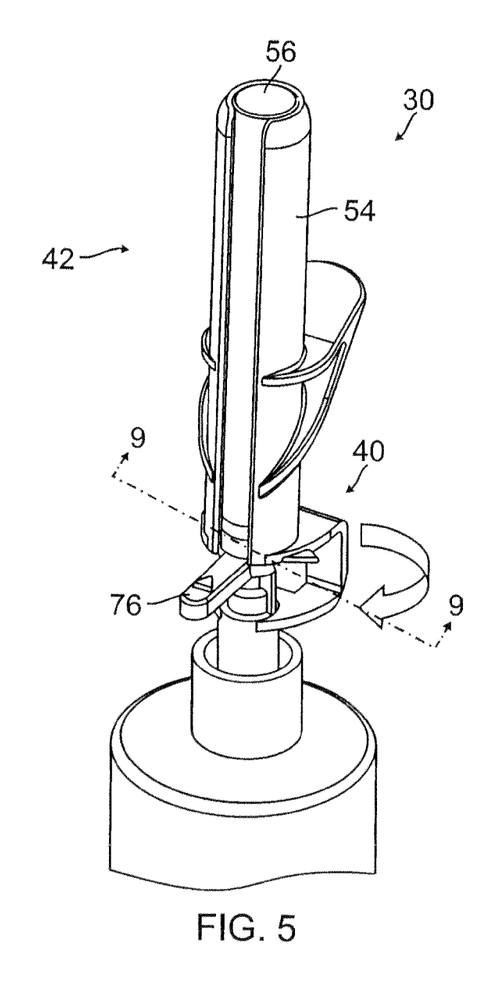
FIG. 5 is a detail front perspective view of a shield of the hinged shield assembly of FIG. 1, showing the shield in a ready-to-use position.
Figure 6:
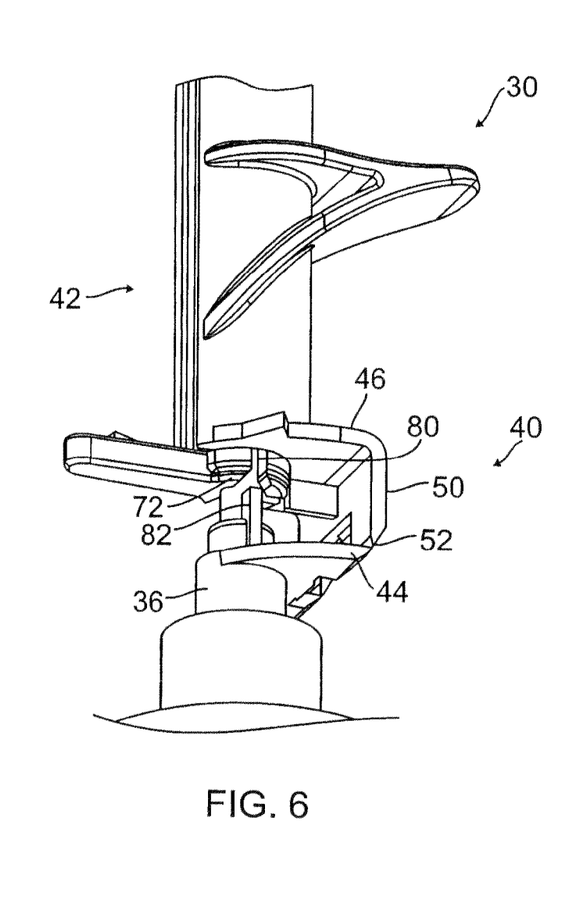
FIG. 6 is a detail lower front perspective view of a shield of the hinged shield assembly of FIG. 1, showing a position of a tab of the shield in the ready-to-use position.
Figure 7:
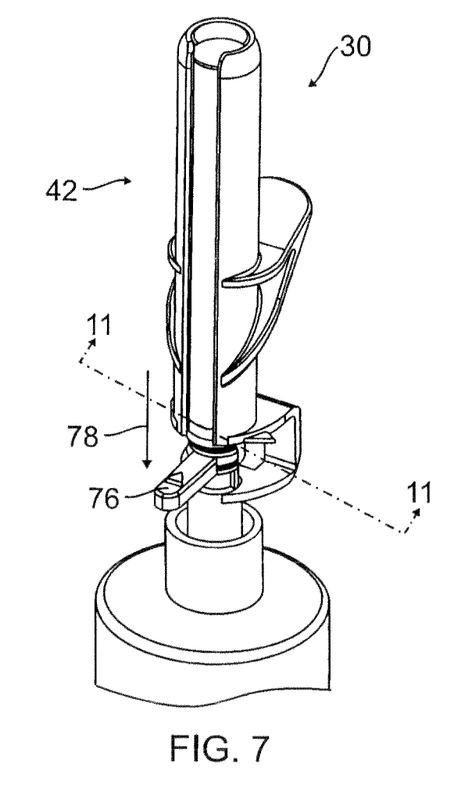
FIG. 7 is a detail front perspective view of a shield of the hinged shield assembly of FIG. 1, showing the shield in a secured position.
Figure 8:
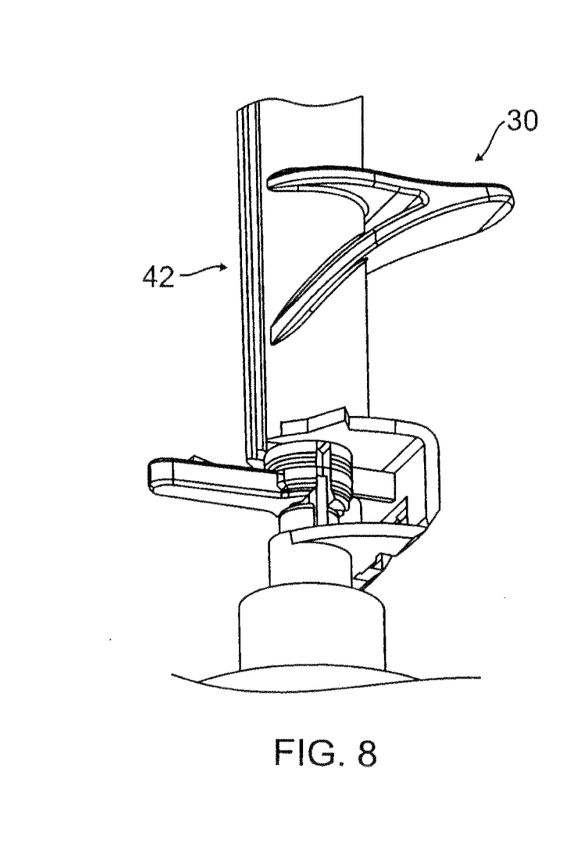
FIG. 8 is a detail lower front perspective view of a shield of the hinged shield assembly of FIG. 1, showing a position of a tab of the shield in the secured position.

FIGS. 1-8 illustrate one embodiment of the present hinged shield assembly 30. The hinged shield assembly 30 cooperates with a syringe 32 (FIGS. 1 and 2) to selectively shield 42 a needle 34 (FIG. 4) extending from a needle hub 36, which engages a distal end 38 of the syringe 32. With reference to FIG. 1, the shield assembly 30 comprises a base 40 and a shield 42 that is pivotable about the base 40. As described in further detail below, the shield 42 is configured to be converted from a packaged or ready-to-use position (FIGS. 5 and 6) to an open position (FIG. 3), and from the open position back to the ready-to-use position and then to a secured position (FIGS. 7 and 8). The ready-to-use position may also be viewed as a temporary lock position because while it prevents the shield 42 from being rotated away from the needle, it can be switched to an open position to permit administration or aspiration of medication. However, a practitioner may leave the needle exposed after filling the syringe and before injecting a patient without moving back to the ready-to-use position.

Figure 3:
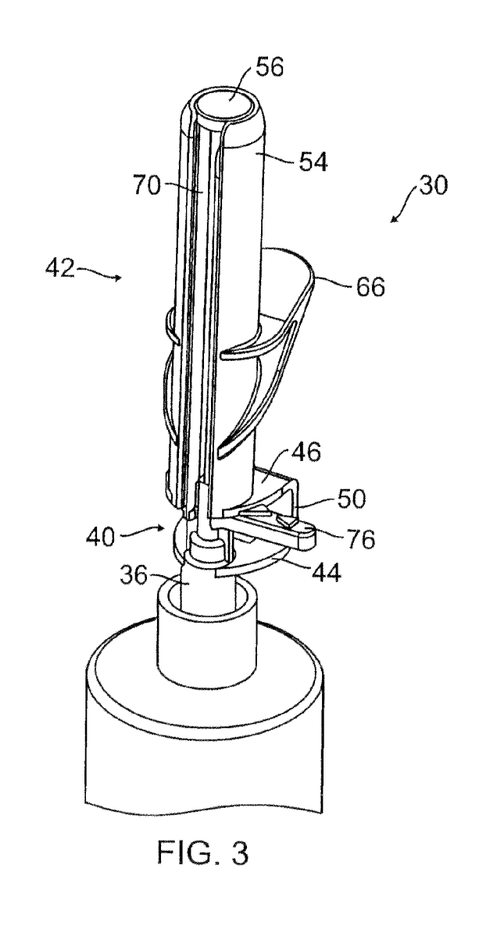
FIG. 3 is a detail front perspective view of a shield of the hinged shield assembly of FIG. 1, showing the shield in an open position.

With reference to FIGS. 3 and 6, the base 40 comprises first and second spaced flanges 44, 46. The first flange 44 extends from the needle hub 36 in a direction substantially perpendicular to a longitudinal axis of the needle 34. The second flange 46 is substantially parallel to the first flange 44, and spaced from the first flange 44 in the distal direction (toward a sharp distal tip 48 of the needle 34 (FIG. 4)). A wall section 50 connects the first and second flanges 44, 46 at edges thereof. A junction of the wall section 50 and the first flange 44 comprises a hinge 52. The shield assembly 30 is pivotable about the hinge 52 between the open position (FIG. 3) and an exposed needle position (FIG. 4), as described in further detail below.

In certain embodiments the shield assembly 30 may be made by injection molding. In such embodiments the base 40 may comprise a single piece, and the hinge 52 may comprise a relatively thin portion of injection-molded plastic, commonly referred to as a "living" hinge. In such embodiments the shield assembly 30 further may be integrally formed as a single unit with the needle hub 36. In other embodiments the shield assembly 30 may be formed separately and secured to the needle hub 36 by known methods, such as welding or mechanical engagement to convert a simple commercially available hypodermic needle into a safety needle assembly.

Figure 2:
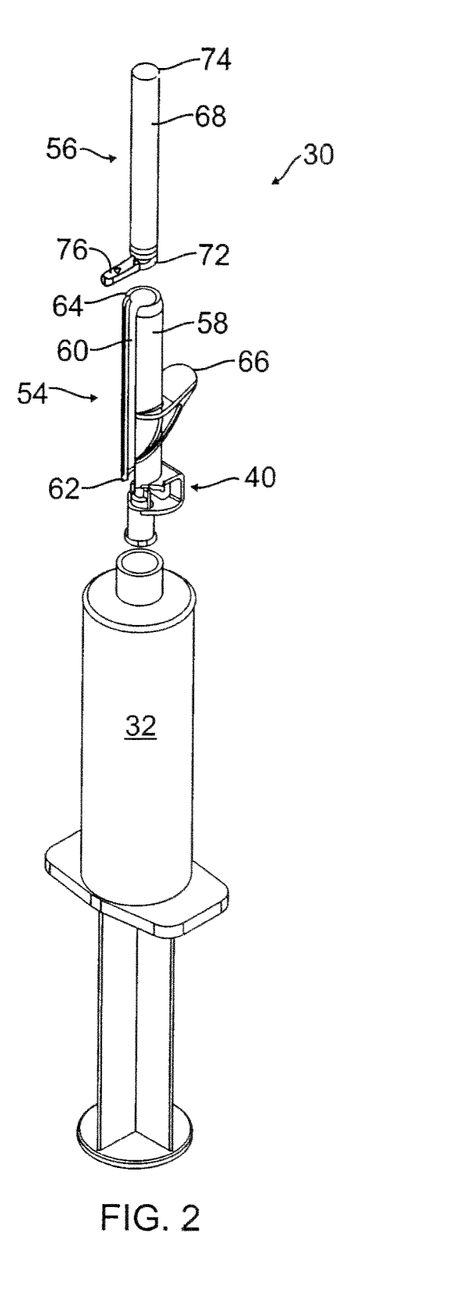
FIG. 2 is a partially exploded front perspective view of the hinged shield assembly of FIG. 1.

With reference to FIG. 3, the shield 42 extends from the second flange 46 in a direction away from the first flange 44. With reference to FIGS. 2 and 3, the shield 42 comprises a first or outer shield 54 and a second or inner shield 56. The first and second shields 54, 56 are rotatable and translatable with respect to one another. For example, the second shield 56 is rotatable with respect to the first shield 54 from the ready-to-use position of FIG. 5 to the open position of FIG. 3. The second shield 56 is further translatable with respect to the first shield 54 from the ready-to-use position of FIG. 5 to the secured position of FIG. 7.

Figure 4:
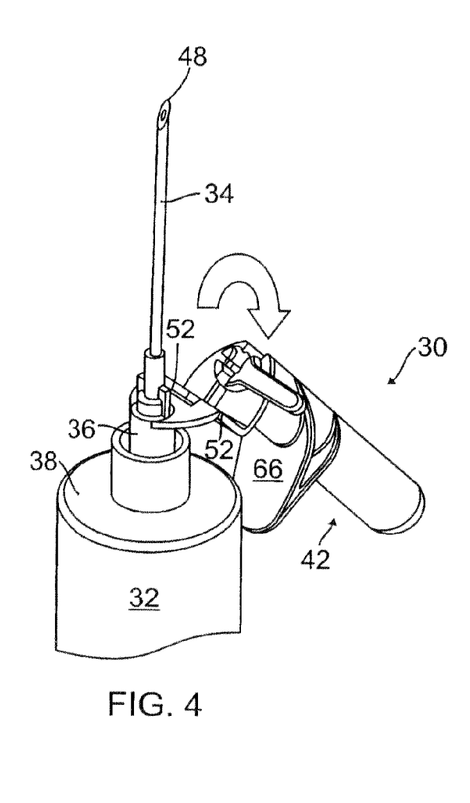
FIG. 4 is a detail front perspective view of a shield of the hinged shield assembly of FIG. 1, showing the shield in an exposed needle position.

With reference to FIG. 2, the first shield 54 is shaped substantially as an elongate, hollow, circular cylinder including a sidewall 58. The sidewall 58 includes a channel 60 that, in the illustrated embodiment, extends in the longitudinal direction from the proximal end 62 to the distal end 64. The distal end 64 of the first shield 54 is open. The first shield 54 further includes a push tab 66 extending from the sidewall 58 opposite the channel 60. The push tab 66 provides a convenient surface for an operator to apply digital pressure to pivot the shield 42 between the open position (FIG. 3) and the exposed needle position (FIG. 4).

With reference to FIGS. 2 and 3, the second shield 56 is shaped substantially as an elongate, hollow, circular cylinder including a sidewall 68. The sidewall 68 includes a channel 70 (FIG. 3) that, in the illustrated embodiment, extends in the longitudinal direction from the proximal end 72 to the distal end 74. The distal end 74 of the second shield 56 is closed, which is preferred although an open end may also be used. The second shield 56 as shown is of the same length as the first shield 54 in that the distal ends of the two shields are generally level or flush. However in an alternative not illustrated embodiment, the second shield 56 can be longer than the first shield 54 so that the distal end 74 of the second shield 56 protrudes out from the distal end 64 of the first shield 54 in the ready-to-use and open positions and is then at least level with the distal end 64 of the first shield 54 in the secure position. This difference provides a caregiver or user with a visual feedback thus enabling the user to more easily determine whether the shield 42 is in the ready-to-use or the secure position. The second shield 56 further includes a tab 76 at the proximal end 62 that extends outward in a direction substantially perpendicular to a longitudinal axis of the second shield 56. In the illustrated embodiment, the tab 76 is spaced approximately ninety-degrees from the channel 70 around the circumference of the second shield 56. However, as those of ordinary skill in the art will appreciate, the tab 76 may occupy substantially any position relative to the channel 70.

With reference to FIG. 5. the first shield 54 substantially surrounds the second shield 56. During manufacture, the second shield 56 is inserted into the first shield 54 through its open distal end 64 (FIG. 2) and translated toward the base 40 until it reaches the ready-to-use position of FIG. 5. In this position. the needle 34 is protected because the sidewall 68 of the second shield 56 interferes with the needle 34 if the shield 42 is pivoted about the hinge 52 (FIG. 6). Said differently, the sidewall 68 of the inner shield blocks the channel 60 of the outer shield thus obstructing the path needed to pivot the shield 42 away from the needle. In certain embodiments, the syringe 32 and shield assembly 30 may be transported from the manufacturer to the customer in the ready-to-use position.

With reference to FIGS. 5-8, the tab 76 provides a convenient surface upon which to apply digital pressure to translate the second shield 56 relative to the first shield 54. Comparing FIGS. 5 and 7. digital pressure applied to the tab 76 in the direction of the arrow 78 translates the second shield 56 relative to the first shield 54 from the ready-to-use position of FIG. 5 to the secured position of FIG. 7. In the secured position the first and second shields 54, 56 are locked against relative translation and rotation. With reference to FIG. 6, the proximal end 72 of the second shield 56 includes a diametrically opposed slot 80 that cooperates with a rib 82 on the needle hub 36 to enable the second shield 56 to translate proximally relative to the first shield 54. When the second shield 56 is rotated away from the ready-to-use position of FIGS. 5 and 6, such as shown in FIGS. 3 and 4, the rib 82 form a barrier that prevents the second shield 56 from translating proximally relative to the first shield 54. However, when the second shield 56 is in the ready-to-use position the ribs 82 align with slots 80 as shown in FIG. 6, and the second shield 56 is able to translate proximally relative to the first shield 54. Accordingly, aspects of the present invention include a provision for aligning sections of the first shield and the second shield for purposes of fixing the needle assembly in a secured position.

Figure 9:
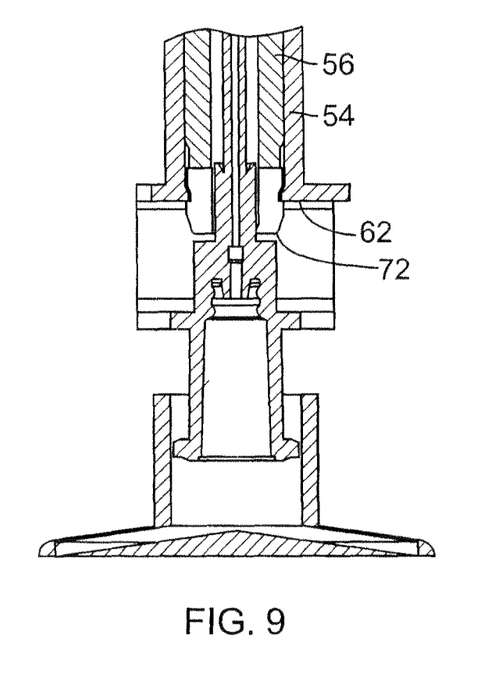
FIG. 9 is a detail front cross-sectional view of the base and proximal portions of the first and second shields of the hinged shield assembly of FIG. 1, taken through the line 9-9 in FIG. 5.
Figure 10:
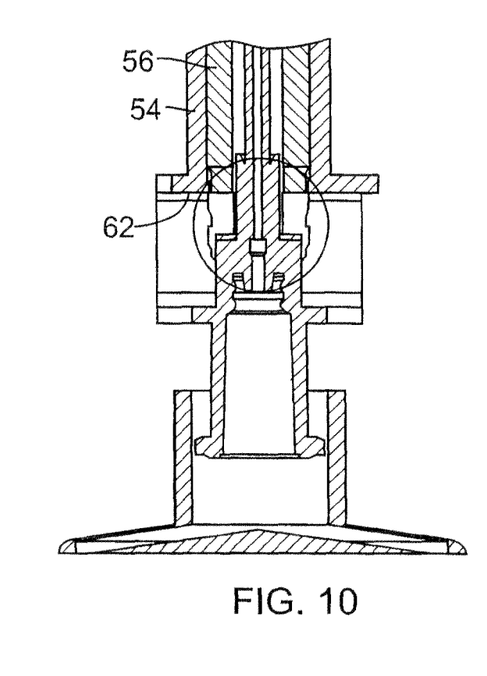
FIG. 10 is a detail front cross-sectional view of the base and proximal portions of the first and second shields of the hinged shield assembly of FIG. 1, taken through the line 11-11 in FIG. 7.
Figure 11:
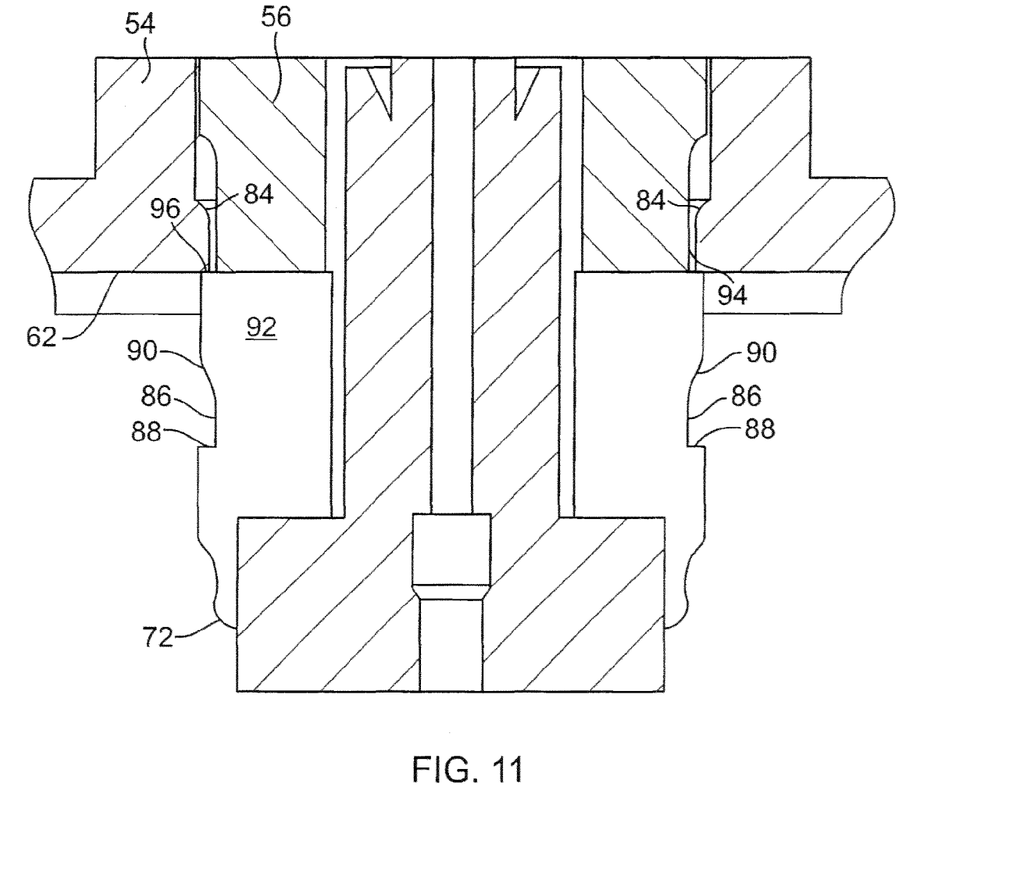
FIG. 11 is a detail view of the area of FIG. 10 contained within the circle 11-11.

FIGS. 9 and 10 show cross-sectional views of the proximal ends 62, 72 of the first and second shields 54, 56 in the ready-to-use position (FIG. 9) and the secured position (FIG. 10). FIG. 11 shows an enlarged detail view of FIG. 10. An inner edge at the proximal end 62 of the first shield 54 comprises a detent 84 that engages a groove 86 in the second shield 56. A ledge 88 at the proximal end of the groove 86 engages the detent 84 to resist translation of the second shield 56 in the distal direction relative to the first shield 54. Similarly, a tapered surface 90 at the distal end of the groove 86 engages the detent 84 to resist translation of the second shield 56 in the proximal direction relative to the first shield 54. The tapered surface 90, however, allows the second shield 56 to translate in the proximal direction relative to the first shield 54 when a threshold digital force is applied to the tab 76. Elastic deformation of the first and second shields 54, 56 enables the relatively larger second shield 56 proximal portion 92 to slide through the relatively smaller opening 94 at the proximal end 62 of the first shield 54. A distal ledge 96 on the second shield 56 eventually passes the detent 84, at which point the materials return to their original shape. In the secured position of FIGS. 10 and 11 the distal ledge 96 on the second shield 56 engages the detent 84 to resist any movement of the second shield 56 in the distal direction relative to the first shield 54. The shields 54, 56 are thus locked against further relative translational motion, and engagement of the rib 82 and slot 80 prevents relative rotational motion.

To use the illustrated needle shield assembly 30, an operator applies digital pressure to the tab 76 to rotate the second shield 56 in a first direction with respect to the first shield 54 from the ready-to-use position of FIG. 5 to the open position of FIG. 3. In the open position the channels 60, 70 on the shields 54, 56 align so that the shield 42 can freely pivot in a first direction from the open position to the exposed needle position of FIG. 4. As the shield 42 pivots about the hinge 52, the needle 34 passes through the aligned channels 60, 70. To pivot the shield 42 about the hinge 52 the operator may apply digital pressure to the push tab 66. In certain embodiments, however, the hinge 52 may be biased toward the exposed needle position so that it springs to that position from the open position without the need to apply digital pressure. In this case a push tab 66 would not be necessary. The digital pressure applied to the tab 76 to rotate the second shield 56 to the open position can also be sufficient to further pivot the shield about the hinge which would also mean that there is no need for a push tab 66. When the shield 42 occupies the exposed needle position, the operator may use the syringe 32 to inject fluid into a patient, or to withdraw fluid from a patient.

Upon completion of fluid injection/withdrawal, the operator pivots the shield 42 back to the open position of FIG. 3. To pivot the shield 42 about the hinge 52 the operator may apply digital pressure to the push tab 66. Then, to secure the shield 42 about the needle 34 he or she applies digital pressure to the tab 76 to rotate the second shield 56 back to the ready-to-use position of FIG. 5. Finally, he or she applies digital pressure to the tab 76 in the direction of the arrow 78 (FIG. 7) to translate the second shield 56 relative to the first shield 54 into the secured position (FIGS. 7 and 8). In the secured position the first and second shields 54, 56 are locked against further rotation or translation relative to one another, as described above. The needle 34 is thus safely contained within the shield 42 where it cannot accidentally prick anyone.

Figure 12:
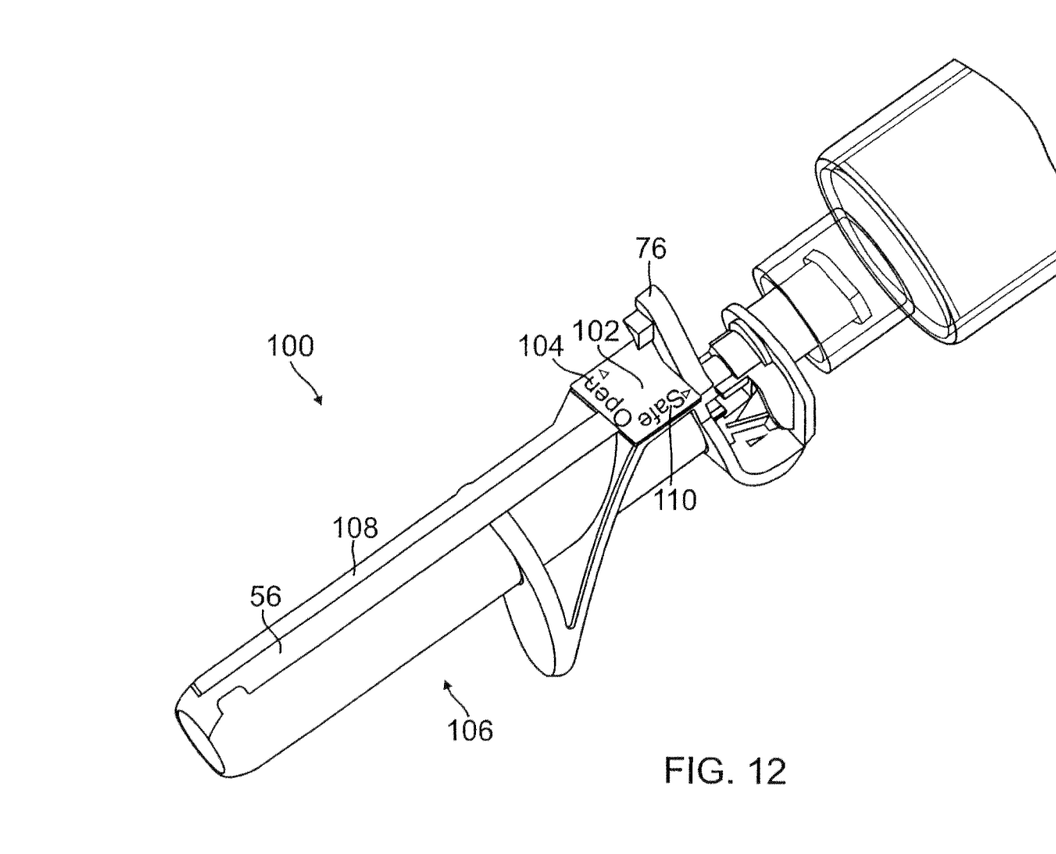
FIG. 12 is a front perspective view of another embodiment of the present hinged shield assembly.

FIG. 12 illustrates another embodiment of the present hinged shield assembly 100. The assembly 100 of FIG. 12 is similar to the assembly 30 of FIGS. 1-11. and includes an indicator 102 that provides a visual aid to the operation of the shield assembly 100. For example, the "Open" indicia 104 tells the operator that to move the shield 106 from the ready-to-use position to the open position he or she must push the tab 76 to rotate the second shield 56 in a first direction with respect to the first shield 108. The "Safe" indicia 110 tells the operator that to move the shield 42 from the ready-to-use position to the secure position he or she must push the tab 76 to translate the second shield 56 in the proximal direction with respect to the first shield 54.

Figure 13:
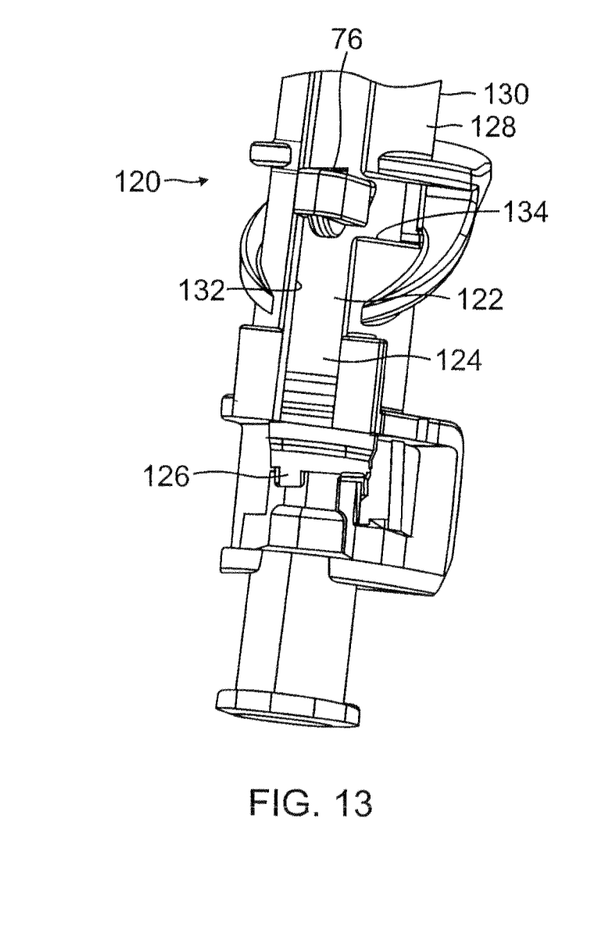
FIG. 13 is a front perspective view of another embodiment of the present hinged shield assembly, showing the shield in a ready-to-use position.
Figure 14:
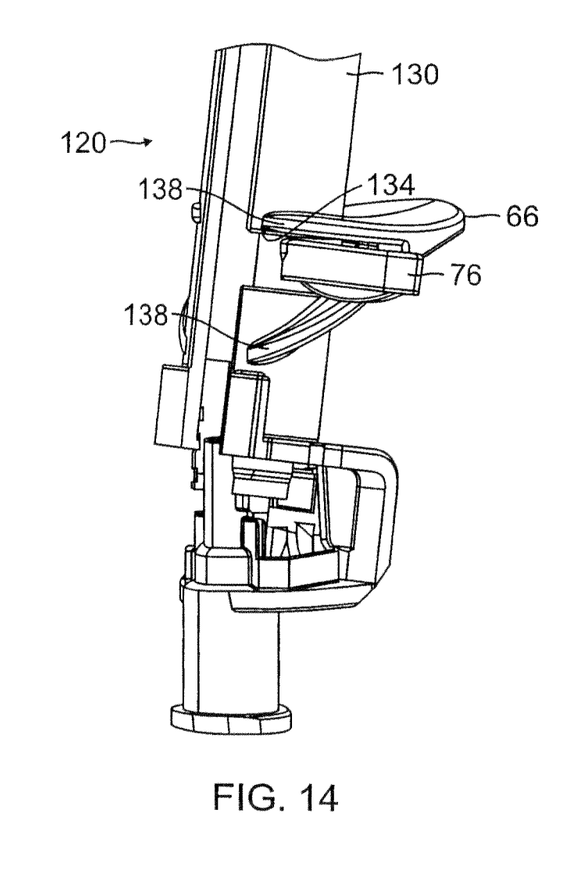
FIG. 14 is a front perspective view of another embodiment of the present hinged shield assembly, showing the shield in an open position.
Figure 15:
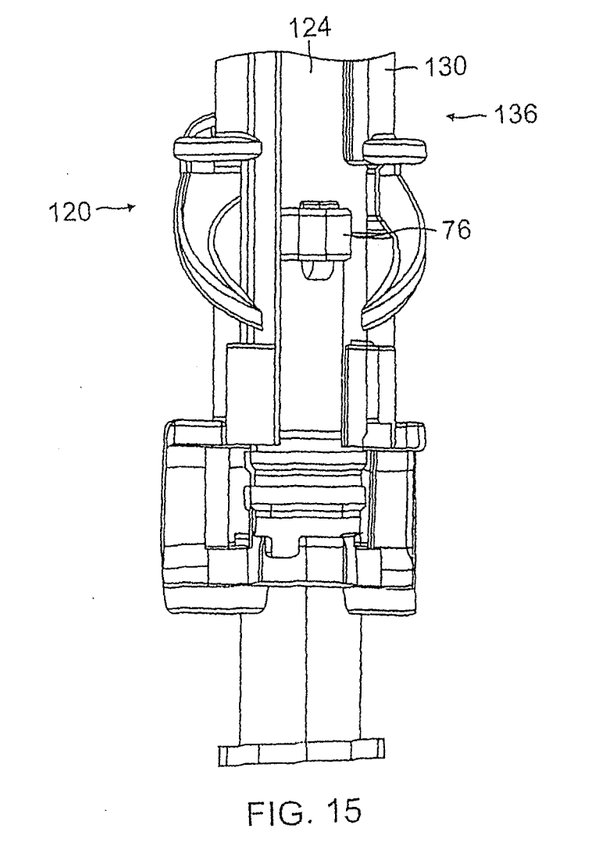
FIG. 15 is a front perspective view of another embodiment of the present hinged shield assembly, showing the shield in a secured position.

FIGS. 13-15 illustrate another embodiment of the present hinged shield assembly 120. The assembly 120 of FIGS. 13-15 is similar to the assembly 30 of FIGS. 1-11. except that the tab 76 is located more distally and somewhere between the distal end and the proximal end. With reference to FIG. 13, the tab 76 extends outward from the sidewall 122 of the second shield 124 at a location that is spaced from the proximal end 126 of the second shield 124. The sidewall 128 of the first shield 130 includes a channel 132. from which a branch 134 that resembles a slot extends around a portion of the circumference of the first shield 130. The branch 134 is located at the same point along the first shield's length as the tab 76 is located along the second shield's length. The second shield 124 can thus be rotated from the ready-to-use position (FIG. 13) to the open position (FIG. 14) by application of digital pressure to the tab 76, which causes the tab 76 to rotate into the branch 134. Also, from the ready-to-use position the second shield 124 can be translated proximally relative to the first shield 130 by application of digital pressure to the tab 76, which moves the shield 136 into the secure position of FIG. 15. In the illustrated embodiment, the branch 134 is located adjacent the push tab 66, and upper and lower fingers 138 of the push tab 66 surround the branch 134 (FIG. 14). In other embodiments, however, the branch 134 may be located at a different position along the first shield's length relative to the push tab 66 at all in which case the digital pressure applied to tab 76 to rotate the second shield 124 to the open position is sufficient to further pivot the shield about the hinge.

As seen best in FIG. 14, the first flange 144 has a projecting rib located on its distal surface that runs in a direction substantially perpendicular to the longitudinal axis of the needle and the wall section 150 that connects the two flanges has a projecting rib which runs in a direction substantially parallel to the longitudinal axis of the needle. Both ribs interact with each other when in the ready-to-use and the secure position to prevent over-rotation of the caps relative to the needle to thereby damage, bend, or distort the needle. Thus, in accordance with aspects of the present invention, ribs are incorporated at the living hinge to prevent the needle from being contacted and deformed by the shields in the event a user applies too much pressure in both of these positions. In other embodiments, other limiting features are used to limit over-rotation. For example, a feature may be incorporated to abut the needle holder to prevent over-rotation.

Figure 16:
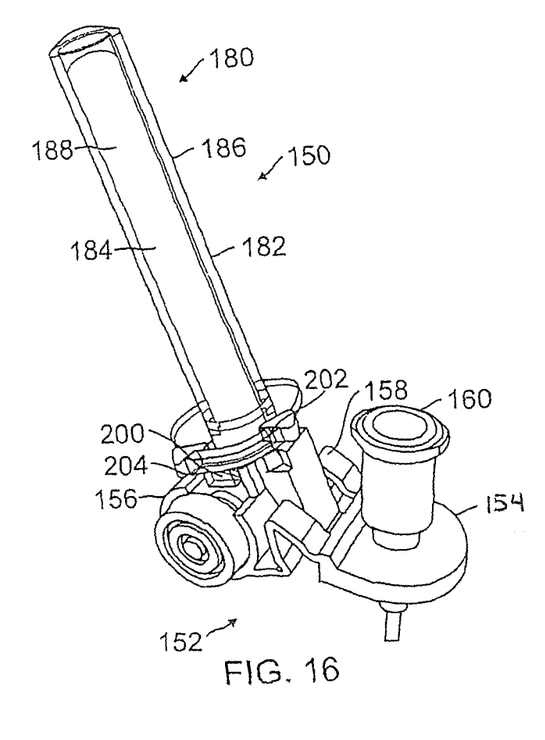
FIG. 16 is a front perspective view of another embodiment of the present hinged shield assembly, showing the shield in an exposed needle position.
Figure 17:
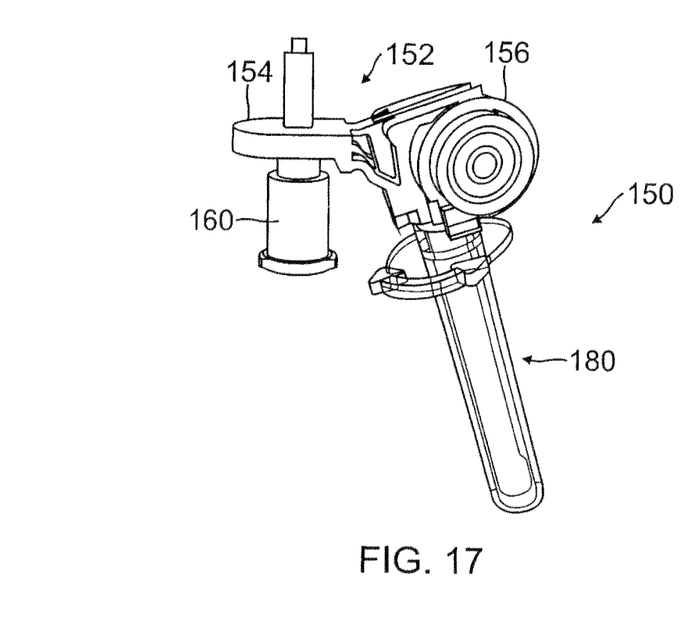
FIG. 17 is a front perspective view of the hinged shield assembly of FIG. 16.
Figure 18:
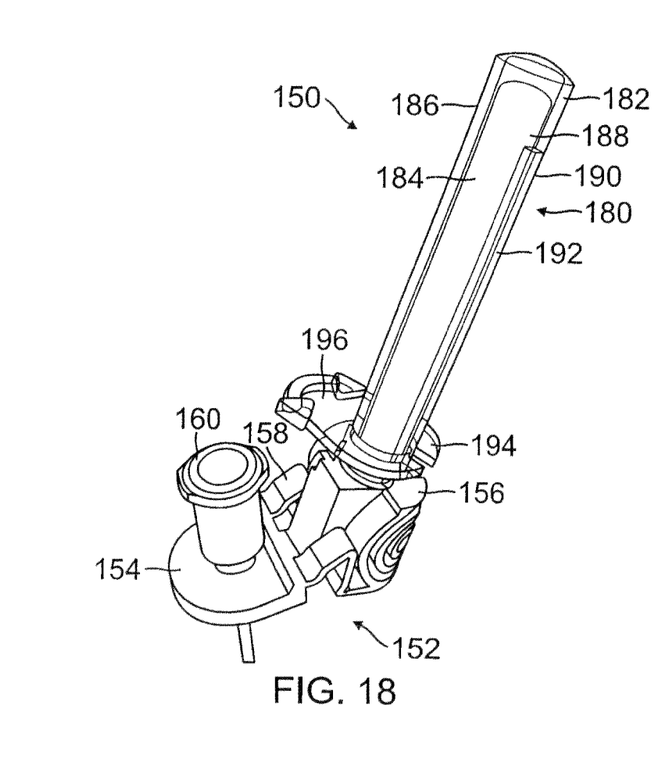
FIG. 18 is a rear perspective view of the hinged shield assembly of FIG. 16.

FIGS. 16-22 illustrate another embodiment of the present hinged shield assembly 150. With reference to FIGS. 16-18, the shield assembly 150 includes a base 152 including a base flange 154 and a button assembly 156 secured to an edge of the flange 154 via a hinge 158. The base flange 154 is substantially planar, and is integrally formed with a needle hub 160 that passes through an approximate center of the flange 154. In certain embodiments, the needle hub 160, base flange 154, hinge 158 and portions of the button assembly 156 may be integrally formed, as by injection molding for example. In such embodiments, the hinge 158 may comprise, as in the illustrated embodiment, a "living" hinge 158. In certain embodiments, the hinge 158, whether living or not, may be biased toward the exposed needle position as explained in further detail below.

Figures 19, 20:
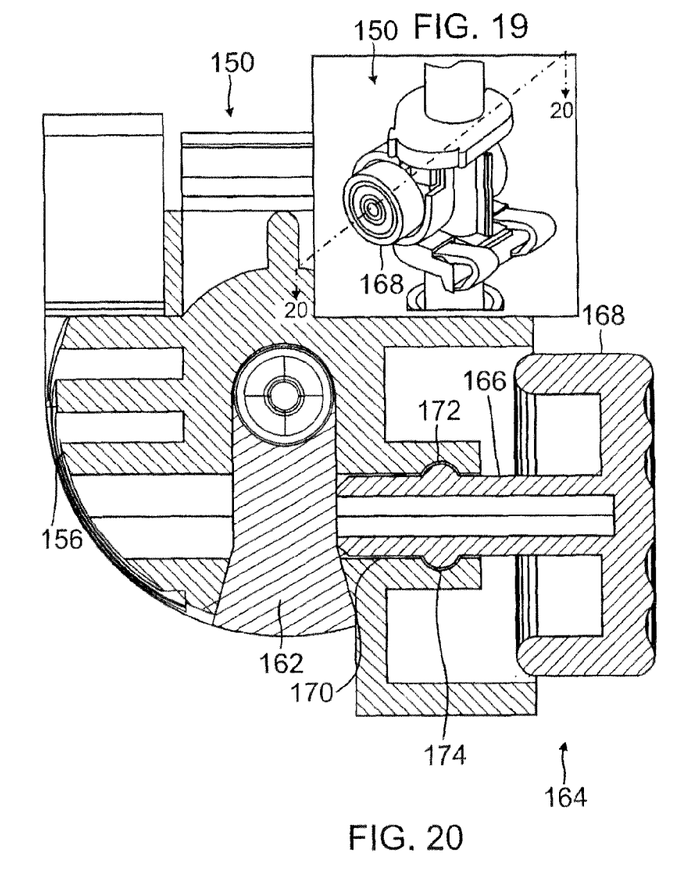
FIG. 19 is a front detail perspective view of the hinged shield assembly of FIG. 16, showing the shield in a ready-to-use position.
FIG. 20 is a top cross-sectional view of the hinged shield assembly of FIG. 16, taken through the line 20-20 in FIG. 19.

With reference to FIGS. 19 and 20, the button assembly 156 comprises a housing 162 and a button 164. The button 164 comprises an elongate stem or rod 166 and a head 168 at a first end of the stem 166. A passageway 170 within the housing 162 receives the stem 166 with the head 168 of the button 164 exposed and located at the side of the housing 162. The stem 166 includes an annular detent 172 that engages a groove 174 in the passageway 170 to resist relative movement of the button 164 and the housing 162. In other embodiments, the detent 172 may not be annular. For example, the detent 172 may comprise one or more semi-spherical protrusions from the stem 166 that engage correspondingly shaped recesses in the passageway 170.

An operator applies digital pressure to the button 164 to overcome a threshold force and dislodge the detent 172 from the groove 174. Elastic deformation of the material from which the detent 172 and/or the housing 162 is constructed allows the button 164 to move from the initial position of FIG. 20 to the depressed position of FIG. 22. When the button 164 is fully depressed, the detent 172 exits the passageway 170 on the far side at which point the detent 172 housing 162 material returns to its initial shape. The detent 172 then engages the edge 176 of the passageway 170 at the far side so that the button 164 remains in the depressed position. The housing 162 includes a button receiving cavity 178 in which the button head 168 is located when it is in the depressed position to prevent unwanted manipulation of the button, such as to reset the button. In this position, the stem 166 extends across the needle 34 (FIG. 22) and prevents the needle 34 from being exposed, as explained in further detail below.

With reference to FIG. 18, the shield assembly 150 further comprises a shield 180 extending from the button assembly 156 in a direction away from the base flange 154. Similarly to the embodiments described above, the shield 180 includes a first or outer shield 182 that at least partially surrounds and encloses a second or inner shield 184. The first and second shields 182, 184 are shaped as elongate, hollow, circular cylinders, and each includes a sidewall 186, 188 having a longitudinal channel 190. 192. The first and second shields 182, 184 are rotatable relative to one another, but are not translatable. A proximal end 194 of the first shield 182 includes a flange 196 that an operator may grip in order to apply a rotating force to the first shield 182.

Like the embodiments of the present hinged shield assembly described above and shown in FIGS. 1-15, the shield assembly 150 of FIGS. 16-22 includes a ready-to-use position (not shown) in which the shield 180 covers the needle 34 and the channels 190, 192 on the first and second shields 182, 184 are not aligned. To use the shield assembly 150 of FIGS. 16-22, an operator rotates the first shield 182 with respect to the second shield 184 so that the two channels 190, 192 are aligned with one another (the open position). In this position, the shield 180 may be pivoted about the hinge 158 to the exposed needle position shown in FIGS. 16-18. Again, the hinge 158 may be biased toward the exposed needle position. or the operator may manually pivot the shield 180 with digital pressure. A tab 200 extending axially at the proximal end of the first shield 182, proximally of the flange 196, is incorporated to abut the button 164 in the packaged and the ready-to-use position to prevent the button 164 from being depressed unintentionally in these positions. The tab 200 is also configured to abut a shoulder 202 of the housing 162 for delimiting the extent of rotation of the first shield. The tab 200 is configured to abut a shoulder 202 of the housing 162 to limit rotation in one direction and a part or edge 204 of the annular wall to limit rotation in the other direction.

Figures 21, 22:
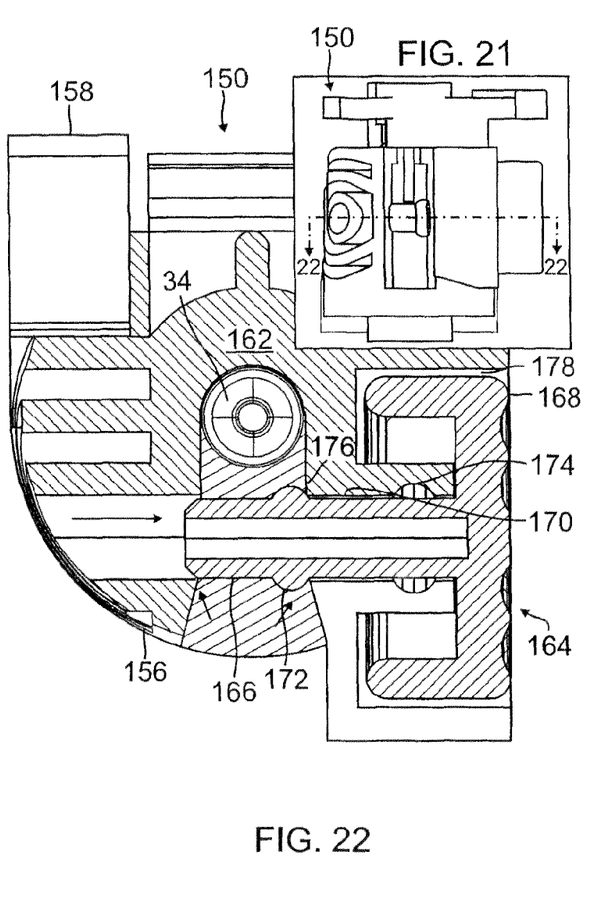
FIG. 21 is a left-side elevation detail view of the hinged shield assembly of FIG. 16, showing the shield in a secured position.
FIG. 22 is a top cross-sectional view of the hinged shield assembly of FIG. 16, taken through the line 22-22 in FIG. 21.

After injecting or withdrawing fluids through the needle 34, the operator pivots the shield 180 back to the open position. In this open position the operator then depresses the button 164 and so secures the shield 180 about the needle 34. With reference to FIG. 22, when the button 164 is depressed the stem 166 extends across the needle 34 on the side of the needle 34 opposite the hinge 158. Thus, the stem 166 forms a barrier that prevents anything but minimal pivoting of the shield 180. In an alternative embodiment, not shown, the tab 200 could be such that it delimits rotational movement of the shields by abutting the shoulder 202 and the edge 204 but does not abut and hinder the button 164 from being depressed in which case the operator can rotate the first shield 182 relative to the second shield 184 to again reach the ready-to-use position in which the needle is fully covered before depressing the button to secure the shield. The advantage of this alternative embodiment over and above the embodiment shown is that the needle is completely covered in the secured position as is also the case with the embodiments shown in FIGS. 1-15. The embodiment shown is however preferable as a tab which prevents the button from being depressed unintentionally in the packaged or ready-to-use position is of greater practical importance.

The above description presents the best mode contemplated for carrying out the present hinged shield assembly and related methods, and of the manner and process of making and using it, in such full, clear, concise, and exact terms as to enable any person skilled in the art to which it pertains to make and use this hinged shield assembly. This hinged shield assembly is, however, susceptible to modifications and alternate constructions from that discussed above that are fully equivalent. For example, the needle may be left exposed after filling the syringe and before injecting the patient without having to move to a ready-to-use position. Additionally, features and aspects discussed for one embodiment may be interchanged and use with another embodiment provided there is no conflict. Consequently, this hinged shield assembly is not limited to the particular embodiments disclosed. On the contrary, this hinged shield assembly covers all modifications and alternate constructions coming within the spirit and scope of the hinged shield assembly as generally expressed by the following claims, which particularly point out and distinctly claim the subject matter of the hinged shield assembly.

What is claimed is:

1. A hinged shield assembly configured to shield a needle to prevent needlesticks, the needle supported by a needle hub comprising a rib, the assembly comprising:
   a base including a hinge; and
   a first shield and a second shield, the first shield extending from the base and at least partially surrounding the second shield, which has a proximal end defining a slot;
   wherein the first and second shields are configured to pivot in a first direction about the hinge, the first and second shields are rotatable about a longitudinal axis of the first shield, the rib is slidably receivable in the slot of the second shield to limit pivoting of the first and second shields about the hinge, and wherein a distal end of the first shield is open.

2. The hinged shield assembly of claim 1, wherein the first shield includes a sidewall and a channel extending along the sidewall in a direction parallel to the longitudinal axis of the first shield.

3. The hinged shield assembly of claim 2, wherein the second shield includes a sidewall and a channel extending along the sidewall of the second shield in a direction parallel to the longitudinal axis of the second shield.

4. The hinged shield assembly of claim 3, wherein the first and second shields are rotatable with respect to one another such that the channels in each may be aligned.

5. The hinged shield assembly of claim 1, wherein the button is round in configuration.

6. The hinged shield assembly of claim 1, wherein the button has a side wall that projects into a button receiving cavity when translated.

7. The hinged shield assembly of claim 1, wherein the stem is hollow.

8. A hinged shield assembly configured to shield a needle to prevent needlesticks, the assembly comprising:
   a base including a hinge defining a pivoting axis;
   a button assembly comprising a button and a stem extending from the button; and
   a first shield and a second shield having a common longitudinal axis, the first shield extending from the base and at least partially surrounding the second shield, the first shield including a sidewall and a channel extending along the sidewall in a direction parallel to the common longitudinal axis, the second shield including a sidewall and a channel extending along the sidewall in a direction parallel to the common longitudinal axis;
   wherein the first and second shields are pivotable about the pivoting axis to expose the needle or to cover the needle, and the first and second shields are rotatable about the common longitudinal axis relative to one another so that the channel of the first shield and the channel of the second shield align; and the button is movable relative to the first shield and the second shield to translate the stem at an angle to the common longitudinal axis to limit pivoting of the first and second shields about the hinge.

9. The hinged shield assembly of claim 8, wherein a distal end of the first shield is open.

10. The hinged shield assembly of claim 8, wherein the button is located on a side opposite the hinge, and the stem is configured to be positioned across a needle extending through the first and second shields.

11. A hinged shield assembly configured to shield a needle to prevent needlesticks, the assembly comprising:
    a base including first and second spaced flanges and a hinge; and
    a first shield and a second shield, the first shield extending from the base and at least partially surrounding the second shield, the first shield having a detent, the second shield defining a groove, a tapered surface at the distal end of the groove, and a ledge at the proximal end of the groove;
    wherein the first and second shields are configured to pivot in a first direction about the hinge, the first and second shields are translatable and rotatable with respect to one another and about a longitudinal axis of the first shield, the detent of the first shield engages the groove of the second shield to resist translation of the second shield in the distal direction relative to the first shield, and the tapered surface allows the detent to translate the second shield in a proximal direction relative to the first shield.

12. The hinged shield assembly of claim 11, wherein the first shield includes a sidewall and a channel extending along the sidewall in a direction parallel to the longitudinal axis of the first shield.

13. The hinged shield assembly of claim 12, wherein the second shield includes a sidewall and a channel extending along the sidewall of the second shield in a direction parallel to the longitudinal axis of the second shield.

14. The hinged shield assembly of claim 13, wherein relative rotation of the first and second shields in a first direction aligns the channels in each.

15. The hinged shield assembly of claim 11, wherein when the first and second shields occupy a first relative rotated position the first and second shields are translatable with respect to one another to lock the second shield against further rotational and translational motion with respect to the first shield.

16. A method of shielding a needle to prevent needlesticks, the method comprising:
    rotating a second shield in a first rotational direction about a needle and a first shield; said first shield extending from a base including first and second spaced flanges and a hinge and at least partially surrounding the second shield; wherein the first shield having a detent, the second shield defining a groove, a tapered surface at the distal end of the groove, and a ledge at the proximal end of the groove; wherein the first and the second shields are pivotable about the hinge; and wherein the first and second shields are translatable and rotatable with respect to one another and about a longitudinal axis of the first shield;

pivoting the first and second shields in a first direction with respect to the needle to expose a sharp distal tip of the needle;

pivoting the first and second shields in a second direction with respect to the needle, opposite the first direction, until the needle is at least partially enclosed within the first and second shields;

rotating the second shield in a second rotational direction, opposite the first rotational direction, about the needle; and translating the second shield relative to the first shield so that a detent engages a groove to lock both the first shield and the second shield against further rotational, pivotal and translational motion with respect to each other and to the needle; the tapered surface allows the detent to translate the second shield in a proximal direction relative to the first shield.

17. The method of claim 16, wherein rotating the second shield in the first direction about the needle aligns a channel on the second shield with a channel on the first shield so that the needle can pass through the two channels during the step of pivoting the first and second shields in the first direction with respect to the needle.

18. The method of claim 17, wherein rotating the second shield in the second direction about the needle moves the channels out of alignment.

19. The method of claim 16, wherein translating the second shield with respect to the first shield comprises applying digital pressure to a tab extending from the second shield.

* * * * *